United States Patent [19]

Tamotu et al.

[11] Patent Number: 4,830,830
[45] Date of Patent: May 16, 1989

[54] APPARATUS FOR DETERMINING BASE SEQUENCE OF NUCLEIC ACID

[75] Inventors: Simada Tamotu, Akishima; Hideki Kambara; Yoshinori Harada, both of Hachioji; Kenichi Watanabe; Jiro Tokita, both of Kokubunji, all of Japan

[73] Assignee: Hitachi, Ltd., Tokyo, Japan

[21] Appl. No.: 829,823

[22] Filed: Feb. 18, 1986

[30] Foreign Application Priority Data

Feb. 25, 1985 [JP] Japan .................. 60-34360

[51] Int. Cl.⁴ .................. G01N 23/06; B01D 59/42
[52] U.S. Cl. .................. 422/71; 204/182.6; 204/299 R; 250/374; 250/562; 356/5; 436/94
[58] Field of Search .................. 204/182.6, 299 R; 356/528, 430; 250/562, 572, 374; 436/94; 422/71, 68

[56] References Cited

U.S. PATENT DOCUMENTS 3,854,587 12/1974 McLoughlin et al. .............. 250/562
4,001,579 1/1977 Lebet .................. 250/572
4,212,541 7/1980 Ducommun et al. .............. 356/430
4,284,491 8/1981 Vesterberg .................. 204/182.8
4,323,439 4/1982 O'Farrell .................. 204/299 R
4,416,762 11/1983 Akiyama .................. 204/299 R
4,501,989 2/1985 Brake .................. 250/374

FOREIGN PATENT DOCUMENTS 60-142243 7/1985 Japan .................. 204/299 R

Primary Examiner—Michael S. Marcus
Attorney, Agent, or Firm—Antonelli, Terry & Wands

[57] ABSTRACT

Nucleic acid fragments labelled by radio isotape migrate at speeds that increase as the molecular weights decrease in a migration path served with a potential at both ends thereof. The migration path is constituted by a pipe-shaped gel support such as a glass tube. A ring-shaped scintillator is provided at a middle portion of the migration path to circumscribe the gel support, and whereby the beta rays are detected. A window may be formed in the glass tube at a portion opposed to the scintillator, so that the beta rays are not attenuated by the glass.

10 Claims, 3 Drawing Sheets

APPARATUS FOR DETERMINING BASE SEQUENCE OF NUCLEIC ACID

BACKGROUND OF THE INVENTION

The present invention relates to an apparatus for determining base sequence of nucleic acid, and particularly to an apparatus for determining base sequence of nucleic acid at high speeds maintaining a high sensitivity by detecting the beta rays emitted from a nucleic acid that is labeled by radio isotope.

So far, the base sequence of nucleic acid has generally been determined relying upon the Maxam-Gilbert method. According to this method, a nucleic acid labeled by radio isotope is chemically cut into fragments, and the fragments of nucleic acid having different lengths are arranged in the order of molecular weights in a gel support sandwiched between glass plates. The gel support is then peeled off from the glass plates, an autoradiogram thereof is photographed to detect an electrophoretic band which includes fragments of radioactive nucleic acid, and whereby the base sequence of nucleic acid is determined.

A conventional method of determining base sequence of nucleic acid fragments based upon the Maxam-Gilbert method will be described below with reference to the drawings. FIG. 1 is a perspective view showing the structure of a conventional electrophoresis apparatus for nucleic acid fragments, which consists of a gel 2 which is sandwiched between two pieces of glass plates 3 and which separates migration of nucleic acid fragments, electrode solution vessels 1a and 1b in which are immersed both ends of the gel 2 which separates migration, and a d-c power source 6. A sample of nucleic acid fragment labeled by radio isotope (e.g., $^{32}P$) is supplied to a slot 5 on the negative pole side of the gel 2 for separating migration, and is allowed to migrate at a voltage Ev of about 40 V/cm per a gel length. Nucleic acid fragments having the same molecular weight form electrophoretic bands 4 heading from the negative pole toward the positive pole, and migrate at migration speeds nearly in reverse proportion to the logarithms of molecular weights. Sequence of nucleic acid bases in the order of molecular weights is determined from the migration pattern of electrophoretic bands 4 of nucleic acid fragments.

In order to read the pattern in this case, it is a generally accepted practice to take a picture of the autoradiogram as mentioned already. With the autoradiogram, however, since the nucleic acid labeled by radio isotope exists in a very small amount, an extended period of time (more than 50 hours) is necessary to transfer it onto an X-ray film, making it difficult to quickly measure various kinds of samples.

In order to compensate the above-mentioned problem of the autoradiogram, it has been contrived to measure the samples at high speeds by directly detecting beta rays from the nucleic acid fragments. FIG. 2 is a section view of the electrophoresis apparatus for this purpose. Namely, beta rays are detected at a moment when the nucleic acid fragment 4 that is migrating passes through the detectors 7, 8, in order to measure the same at a high speed without using any autoradiogram. According to this method, as will be understood from FIG. 2, beta rays incident on the detector 7 of one side are detected by the detector 7 only, and an extended period of time is required to take a measurement maintaining a high S/N ratio. By using two detectors 7, 8 to take measurements from both sides of the glass plates, furthermore, the amount of incident beta rays is doubled. However, beta rays in a direction perpendicular to the surface of the paper are not measured.

SUMMARY OF THE INVENTION

The object of the present invention is to provide an apparatus for determining base sequence of nucleic acid at a higher speed maintaining an increased accuracy.

The present invention has been accomplished in order to solve a problem that the existing autoradiogram is simply utilizing a portion of beta rays emitted from the nucleic acid fragments. The present invention further attempts to solve a problem that the traditional method of directly detecting beta rays is not sufficiently detecting the beta rays emitted from the nucleic acid fragments.

According to the present invention, therefore, nucleic acid fragments are migrated in a cylinder-shaped gel, and a ring-shaped scintillator is provided to surround the gel, in order to effectively detect all of the beta rays emitted from the nucleic acid fragments. This makes it possible to take measurement maintaining a higher sensitivity than the conventional autoradiogram, and to determine base sequence of nucleic acid at a high speed.

DETAILED DESCRIPTION OF THE PREFERRED EMBODIMENTS

An embodiment of the present invention will be described below in conjunction with the drawings.

Figure 1:
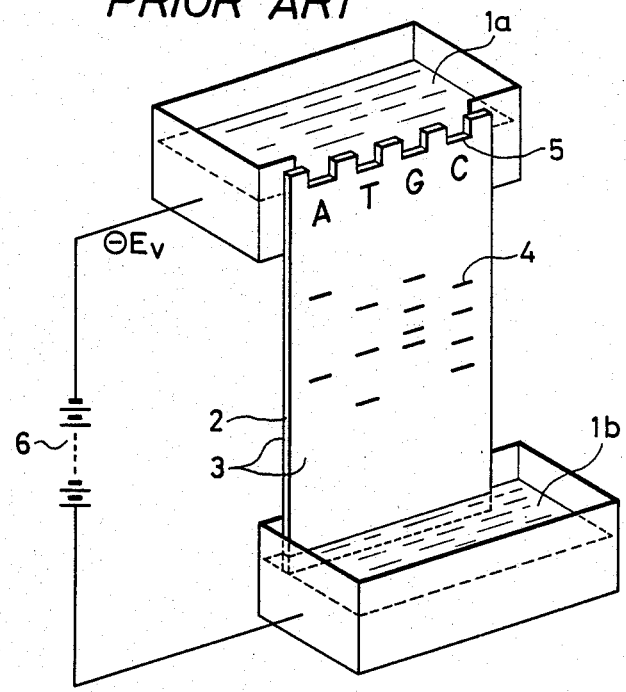
FIG. 1 is a perspective view showing a conventional apparatus for electrophoresis.
Figure 2:
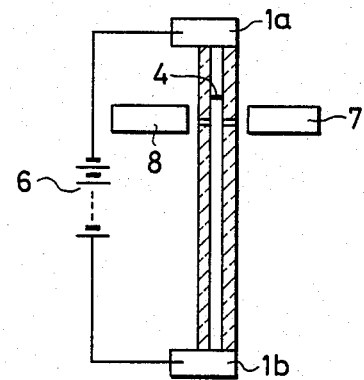
FIG. 2 is a vertical section view of a migration path in a conventional apparatus for electrophoresis.
Figure 3:
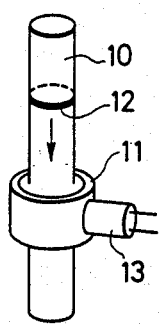
FIG. 3 is a perspective view of a cylinder-shaped gel and a ring-shaped scintillator according to an embodiment of the present invention.

FIG. 3 is a diagram which illustrates the structure of a cylinder-shaped gel 10 and a ring-shaped scintillator 11 according to an embodiment of the present invention. In this case, the smaller the molecular weight, the greater the speed at which a nucleic acid fragment 12 migrates through the gel 10. The beta rays emitted in all directions from the radio isotope labeled onto the nucleic acid fragment are converted into fluorescence by the scintillator 11, subjected to the photoelectric conversion by a photomultiplier tube 13, and are detected as an electric current.

Figure 4:
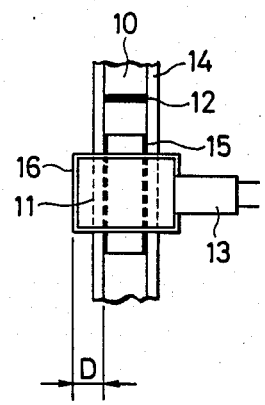
FIG. 4 is a section view of the structure of FIG. 3.

FIG. 4 is a section view which concretely illustrates a relation between the cylinder-shaped gel 10 and the ring-shaped scintillator 11 that are shown in FIG. 3. The cylinder-shaped gel 10 is contained in a glass tube 14. The scintillator 11 circumscribes the glass tube 14; i.e., the two may be intimately contacted to each other or may leave a gap therebetween. The beta rays from the nucleic acid fragment 12 attenuate through the glass tube 14. In order that the beta rays are emitted to the scintillator 11, therefore, a portion of the glass tube 14 corresponding to the scintillator 11 is constituted, for example, by a film 15. Therefore, the beta rays emitted in all direction are detected as the nucleic acid fragment 12 undergoes the electrophoresis and pass through the scintillator 11.

The gel 10 contains acrylamide in an amount of, for example, 8 to 12%, and assumes the shape of a cylinder having a diameter of about 0.5 mm to 5 mm. The glass tube 14 forms the gel 10, and has an inner diameter of 0.5 mm to 5 mm, and a thickness of 2 mm. The film 15 should be composed of a material which has enough strength to support the gel instead of the glass tube 14 and which permits the beta rays to pass through sufficiently. For this purpose, the film 15 will suitably be composed of, for example, a polyester resin. The scintillator 11 should suitably be a plastic scintillator having a thickness D of 10 mm, which emits fluorescent light, which exhibits a high sensitivity for the beta rays, and which absorbs a maximum energy, 1.7 MeV, of radio isotope (e.g., $^{32}P$) without permitting the leakage of beta rays. The plastic scintillator permits light to pass through. Therefore, the plastic scintillator should be covered with a thin aluminum film to shield external light, and to guide the fluorescent light into the photomultiplier tube 13 without permitting it to escape. Therefore, the beta rays from the nucleic acid fragment 12 migrating through the cylinder-shaped gel 10 can be measured throughout the whole angle of 360 degrees in directions at right angles with the direction of migration.

Figure 5A:
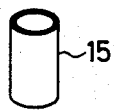
FIG. 5(a) is a view showing the structure of a tube and FIG. 5(b) is a view showing the structure of a glass tube which constitutes a migration path and a detector portion.
Figure 5B:
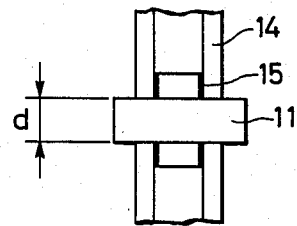

FIG. 5(b) illustrates in detail the method of constituting the glass tube 14 and the film 15 of FIG. 4. First, a polyester resin is molded into a tube as shown in FIG. 5(a). The film tube 15 is adhered onto the inner surface of the glass tube 14 in order to form a pipe. In this case, the thickness of the scintillator 11 defines the width of slit of the detector portion. If the thickness and gap of the nucleic acid fragment are taken into consideration, however, the scintillator should have a thickness d over a range of 0.5 to 2 mm.

Figure 6:
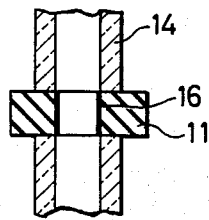
FIG. 6 is a view showing another structure of the glass tube and the detector portion.

As shown in FIG. 6, furthermore, if the inner surface of the scintillator 11 is coated with a polyester film or with a suitable material such as silicon 16 that matches with the gel, the scintillator 11 and the glass tube 14 can be combined together with a simple structure.

Figure 7:
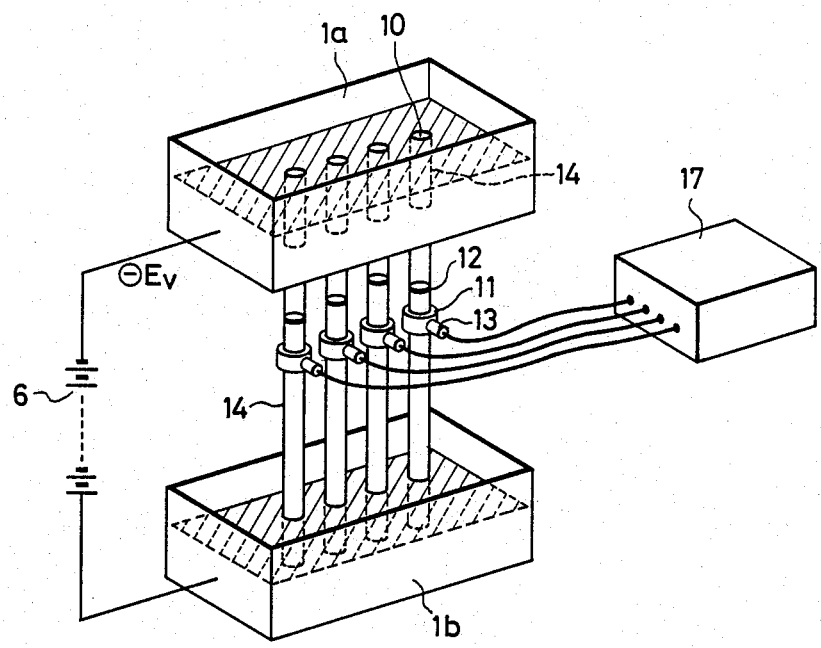
FIG. 7 is a view showing the whole structure of an apparatus for electrophoresis according to an embodiment of the present invention.

Described below is a method of detecting electrophoresis by the cylinder-shaped gel and the scintillator in conjunction with FIG. 7. The cylinder-shaped gel 10 formed in the glass tube 14 has one end that is immersed in a solution contained in the upper migration vessel 1a and has the other end that is in contact with the lower migration vessel 1b. If a voltage is directly applied across the upper and lower migration vessels 1a and 1b, the nucleic acid fragment 12 supplied to the cylinder-shaped gel 10 undergoes electrophoresis from the negative pole toward the positive pole as shown in FIG. 7. When the nucleic acid sample passes through the scintilator 11, the beta rays from the sample are converted into fluorescence by the scintillator. Namely, the nucleic acid fragment 12 is detected through the photomultiplier tube 13 and a pulse counting circuit 17.

Figure 8:
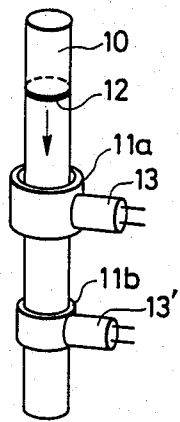
FIG. 8 is a view showing another embodiment of the present invention.

In the embodiment of FIG. 7, the nucleic acid fragment 12 is measured by providing one ring-shaped scintillator 11 for one cylinder-shaped gel 10. However, a plurality of scintillators 11a, 11b may be provided for one cylinder-shaped gel 10 as shown in an embodiment of FIG. 8, to obtain an additional merit from the standpoint of detection. For instance, the beta rays from the same nucleic acid fragment 12 can be counted twice as much by the two scintillators 11a, 11b, to effectively measure the nucleic acid fragment of a very small amount. As described with reference to FIG. 5b, furthermore, the width of slit of the detector portion can be equivalently changed by changing the thickness of the scintillator 11. If the scintillators 11a and 11b are constituted to have different thicknesses, therefore, the nucleic acid fragment 12 can be measured maintaining a high space resolution and a high sensitivity.

In the embodiments of FIGS. 3 to 8, the gel assumed the shape of a cylinder. The same effects, however, can also be obtained even with the gel of the shape of a prism or a square pole. When the gel of the shape of a square pole is used, the inner periphery of the scintillator can be formed in a square shape more easily than a circular shape. From the standpoint of loss of light transmission, however, the outer periphery of the scintillator should be formed in a circular shape.

The cylindrical gel of the present invention exhibits better thermal conductivity than the conventional plate-type gel, and develops little distortion in the migration pattern that results from nonuniform temperature. This fact helps solve the assignment for correcting the distortion of migration pattern in the system for directly detecting the beta rays.

In FIG. 7, the portion of glass tube 14 below the scintillator 11 and the detector 13 is contacted to the electrode solution vessel 1b. According to the present invention, however, the lower portion of the glass tube 14 may be omitted. That is, the nucleic acid fragment that migrates is measured when it passes over the detector 13 and its presence is stored in the pulse counting circuit 17. Therefore, the nucleic acid fragment 12 may be permitted to flow directly into the vessel 1bof electrode solution. With the conventional art, the nucleic acid fragment had to be spread over a wide range to obtain an autoradiogram thereof. According to the present invention, on the other hand, the nucleic acid fragments can be analyzed in quantities irrespective of the length of gel, provided the fragments undergo migration even by small amounts at dissimilar speeds in the order of molecular weights.

According to the present invention as described above in detail, the beta rays from the nucleic acid fragment are measured over a wide solid angle to greatly improve the reliability of analysis. Furthermore, since the beta rays are measured in large amounts, the count number of beta rays equal to that of the conventional art can be obtained in a short period of time, making it possible to detect the sample at high speeds. When the fragment is obtained only in small amounts due to an unstable pre-treatment system for obtaining nucleic acid fragments, the beta rays are obtained in samll amounts. According to the present invention, however, even the fragment of a small amount can be measured maintaining high reliability.

What is claimed is:

1. An apparatus for determining base sequence of nucleic acid, comprising:

a pipe-shaped gel supoprt which contains a gel and which constitutes a migration path for nucleic acid fragments labeled by radio isotope;

electrode solution layers installed at both ends of said gel support;

a power source for applying potential across said electrode solution layers;

means for photoelectric conversion; and a ring-shaped radiation detector for detecting radioactive emissions, converting the detected emissions to light and guiding the generated light to said means for photoelectric conversion, said ring-shaped radiation detector being provided to circumscribe said gel support at a middle portion thereof and being intimately contacted thereto or spaced therefrom to form a gap therebetween.

2. An apparatus for determining base sequence of nucleic acid according to claim 1, wherein said ring-shaped radiation detector is a plastic scintillator and is covered with a thin aluminum film to shield external light.

3. An apparatus for determining base sequence of nucleic acid according to claim 1, wherein the ring-shaped radioactive ray detector is a ring-shaped plastic scintillator which exhibits a high sensitivity to beta rays, emits fluorescent light and absorbs 1.7 MeV of radio isotope without permitting leakage of beta rays.

4. An apparatus for determining base sequence of nucleic acid according to claim 3, wherein said ring-shaped plastic scintillator is covered with a thin aluminum film to shield external light.

5. An apparatus for determining base sequence of nucleic acid according to claim 1, wherein said migration path is constituted by a plurality of pipe-shaped gel supports and each of said pipe-shaped gel supports is circumscribed at a middle portion thereof with at least one radioactive ray detector having a ring-shaped scintillator.

6. An apparatus for determining base sequence of nucleic acid according to claim 1, wherein said ring-shaped radiation detector is a plastic scintillator.

7. An apparatus for determining base sequence of nucleic acid according to claim 1, wherein said means for photoelectric conversion is a photo-multiplier tube.

8. An apparatus for determining base sequence of nucleic acid according to claim 1, wherein said ring-shaped radiation detector is a plastic scintillator and said means for photoelectric conversion is a photo-multiplier tube.

9. An apparatus for determining base sequence of nucleic acid according to claim 1, wherein said radioactive emissions are beta rays and said ring-shaped radiation detector converts said beta rays into fluorescent light and guides said fluorescent light to said means for photoelectric conversion.

10. An apparatus for determining base sequence of nucleic acid according to claim 9, wherein said means for photoelectric conversion is a photo-multiplier tube.

* * * * *